United States Patent [19]

Elbe et al.

[11] 4,388,465
[45] Jun. 14, 1983

[54] PREPARATION OF PHENOXY-AZOLYL-BUTANONE DERIVATIVES

[75] Inventors: Hans-Ludwig Elbe; Hermann Arold; Eckart Kranz; Claus Stölzer, all of Wuppertal, Fed. Rep. of Germany

[73] Assignee: Bayer Aktiengesellschaft, Leverkusen, Fed. Rep. of Germany

[21] Appl. No.: 300,071

[22] Filed: Sep. 8, 1981

[30] Foreign Application Priority Data

Sep. 17, 1980 [DE] Fed. Rep. of Germany ....... 3035022

[51] Int. Cl.³ .................. C07D 233/60; C07D 249/08
[52] U.S. Cl. ..................................... 548/262; 548/341
[58] Field of Search ................................ 548/262, 341

[56] References Cited

U.S. PATENT DOCUMENTS 4,013,677 3/1977 Stolzer et al. ...................... 548/262

FOREIGN PATENT DOCUMENTS 358031 11/1980 Austria .
11191 5/1980 European Pat. Off. .
2201063 6/1977 Fed. Rep. of Germany .
2406665 3/1978 Fed. Rep. of Germany .
2743767 4/1979 Fed. Rep. of Germany .

OTHER PUBLICATIONS

Methoden Der Organischen Chemie, (Houben-Weyl), Eugen Müller, Band VII/2b Ketone Teil II, 1976, pp. 1491-1497.
Lehrbuch Der Organischen Chemie, Prof. Dr. Hans Beyer, S. Hirzel Verlag Leipzig, 1958, p. 150.

Primary Examiner—Alton D. Rollins
Attorney, Agent, or Firm—Sprung, Horn, Kramer & Woods

[57] ABSTRACT

In the preparation of a phenoxy-azolyl-butanone derivative of the formula

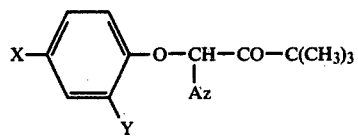

in which
X is a halogen atom,
Y is a hydrogen or halogen atom, and
Az is an imidazolyl radical or a 1,2,4-triazolyl radical, wherein dichloropinacolin of the formula

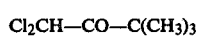

is reacted with an azole of the formula

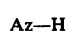

and a phenol of the formula

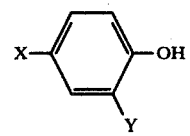

in the presence of an acid-binding agent, the improvement which comprises carrying out the reaction in the presence of a water-immiscible organic solvent at a temperature between about 40° and 150° C., adding to the solvent at a temperature between about 0° and +80° C. a mineral acid, thereby to precipitate the mineral acid salt of the phenoxy-azolyl-butanone derivative, and separating such salt. Surprisingly the product does not hydrolyze when standing in contact with the mineral acid solution. The product is a known fungicide.

9 Claims, No Drawings

PREPARATION OF PHENOXY-AZOLYL-BUTANONE DERIVATIVES

The present invention relates to an unobvious process, which can be used industrially, for the preparation and purification of certain known phenoxy-azolylbutanone derivatives.

It has already been disclosed that phenoxy-azolyl-butanone derivatives can be obtained when dihalogenopinacolins are reacted with 1,2,4-triazole and phenols in the presence of an acid-binding agent (such as potassium carbonate) and in the presence of a polar solvent (such as acetone) at temperatures between 0° and 150° C. (see our DE-AS (German Published Specification) No. 2,406,665).

However, this process has the disadvantage that, especially in the case of the preparation on an industrial scale, competing reactions lead to the increased formation of by-products which considerably reduce the content of the desired end product. In addition, the space/time yield is unsatisfactory because of a troublesome and time-consuming working up procedure.

The present invention now provides a process for the preparation of a phenoxy-azolyl-butanone derivative of the general formula

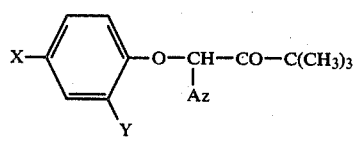   (I)

in which
X represents a halogen atom,
Y represents a hydrogen or halogen atom and
Az represents an imidazolyl radical or 1,2,4-triazolyl radical,
in which dichloropinacolin of the formula

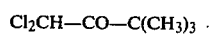   (II)

is reacted with an azole of the general formula

   (III)

in which
Az has the meaning given above, and a phenol of the general formula

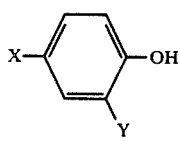

in which
X and Y have the meaning given above, in the presence of an acid-binding agent, characterized in that the reaction is carried out in the presence of a water-immiscible organic solvent at a temperature between about 40° and 150° C., the crude end product of the formula (I) is left in solution, without changing the solvent, and, for purification of the product, in the same solution, a mineral acid is added at a temperature between 0° and +80° C., the salt is separated off and the pure end product of the formula (I) is isolated from the salt. The process of the present invention gives the phenoxy-azolyl-butanone derivatives of formula (I) in good yield and purity, even on an industrial scale.

It is surprising that the phenoxy-azolyl-butanone derivatives of the formula (I), which are O,N-acetals, are stable in the presence of mineral acid under the precipitation conditions (at 0° to 80° C.), as it is generally known that O,N-acetals can easily be split by acid catalysts. This is all the more surprising since the salt of the compound of the formula (I) does not precipitate instantaneously, but is exposed to attack by excess mineral acid for some time.

It is also surprising that the water-immiscible ketones (such as methyl isobutyl ketone), preferably to be used as organic solvents for the procedure according to the invention, can be employed for the salt precipitation. In particular, it is generally known that, for example, acetone, as a solvent which is structurally comparable to methyl isobutyl ketone, very readily undergoes condensation reactions under the catalytic influence of mineral acids, such as, in particular, of the sulphuric acid which is preferably to be used according to the invention. The stability of methyl isobutyl ketone in the presence of concentrated sulphuric acid in the temperature range of 0° to 80° C. to be used was thus hardly to be expected.

The procedure, according to the invention, by which the process is carried out has the advantages that the desired product is obtained with a content of <97%, even in the case of preparation on an industrial scale, and at the same time the space/time yield is good.

In the general formula I, X preferably represents a chlorine atom, Y preferably represents a hydrogen or chlorine atom and Az preferably represents the 1,2,4-triazol-1-yl radical.

The process can preferably be carried out by the following procedure: 1 to 1.5 Kmoles of dichloropinacolin and 1 to 4 Kmoles of acid-binding agent in a water-immiscible ketone (such as methyl isobutyl ketone) or an aromatic hydrocarbon (such as toluene) are reacted with a mixture of 1 to 1.5 Kmoles of azole(1,2,4-triazole or imidazole) and 1 Kmole of a phenol (such as 4-chlorophenol) at 40° to 120° C. This method of addition is preferred; however, it is also possible to initially introduce the phenol, the azole and the acid-binding agent and to add dichloropinacolin. The reaction time is 8 to 15 hours. For working up, water is added to the reaction mixture and the phases are then separated. The organic phase, which contains the desired reaction product, is washed with dilute sodium hydroxide solution for further removal of undesired by-products. After renewed phase separation, mineral acid (such as sulphuric acid) is added to the organic phase at 0° to 80° C.

The salt is separated off and the free base of the formula (I) is obtained therefrom in the customary manner with a content of >97% (determined by gas chromatography).

Possible water-immiscible organic solvents are, in particular: methyl isobutyl ketone or other water-immiscible ketones.

It is furthermore also possible to use other water-immiscible solvents, such as aromatic hydrocarbons. Examples which may be mentioned are: toluene, xylene and chlorobenzene.

Possible acid-binding agents for the rection are any of the customary organic and, in particular, inorganic acid-binding agents. Examples which may be mentioned are: tertiary amines (such as triethylamine or dimethylcyclohexylamine), alkali metal hydroxides (such as sodium hydroxide or potassium hydroxide), alkali metal carbonates (such as sodium carbonate or potassium carbonate), and alkaline earth metal hydroxides or carbonates (such as calcium hydroxide or calcium carbonate).

Sulphuric acid, for example concentrated sulphuric acid, is preferably used as the mineral acid required for separating out the salt in the process according to the invention.

The reaction is carried out at a temperature between about 40° and 150° C., preferably at a temperature between about 40° and 120° C.

The purification step according to the invention is carried out at a temperature between about 0° and 80° C., preferably at a temperature between about 20° and 70° C.

In carrying out the reaction, 1 to 1.5 Kmoles of dichloropinacolin, 1 to 1.5 Kmoles of the azole and 1 to 4 Kmoles of acid-binding agent are preferably employed per Kmole of phenol.

The compounds of the formula (I) have a very good fungicidal activity (see U.S. patent application Ser. No. 3,912,752). They can be used, for example, with particularly good success as agents against powdery mildew (as leaf fungicides) and against cereal diseases, such as cereal rust (as a seed dressing).

The process according to the invention (with a comparison with the state of the art) is illustrated in the following preparative example: Preparative Example on an industrial scale

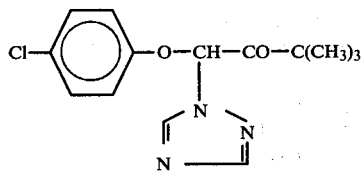

(a) process according to the invention 197 kg (1,165 moles) of dichloropinacolin and 420 kg (3,040 moles) of potassium carbonate in 640 kg of methyl isobutyl ketone were warmed to 90° C. in a 3,000 liter stirred kettle. A mixture of 129 kg (1,000 moles) of 4-chlorophenol and 76.4 kg (1,100 moles) of 1,2,4-triazole was added to the kettle. The mixture was subsequently stirred at 90° to 95° C. for 10 hours and cooled to 50° C. and 1,400 kg of water were added. The mixture was subsequently stirred for 30 minutes and the aqueous phase was then separated off. The organic phase was washed with 350 kg of dilute sodium hydroxide solution and then with 50 kg of water.

76 kg of 96% strength sulphuric acid were allowed to run in at 40° C. and the mixture was then cooled to 10° C. The precipitate which had separated out was washed with 300 kg of methyl isobutyl ketone and hydrolyzed in a mixture of 400 kg of methyl isobutyl ketone, 400 kg of water and 100 kg of 45% strength sodium hydroxide solution. The aqueous phase was separated off and the organic phase was concentrated. 183 kg (61% of theory, relative to the 4-chlorophenol employed) of 1-(4-chlorophenoxy)-3,3-dimethyl-1-(1,2,4-triazol-1-yl)-butan-2-one with a melting point of 75° to 76° C. and a content of 97.5% (determined by gas chromatography) were obtained.

(b) known process (batch on an industrial scale in accordance with the instructions of U.S. patent application Ser. No. 4,013,677.

550 kg of acetone were initially introduced into a 3,000 liter stirred kettle. 104 kg (1,500 moles) of 1,2,4-triazole, 634 kg (4,600 moles) of potassium carbonate and 193 kg (1,500 moles) of 4-chlorophenol were added, while stirring. The mixture was heated to the reflux temperature, and 330 kg (1,950 moles) of dichloropinacolin, dissolved in 240 kg of acetone, were added. When the addition had ended, the mixture was stirred under reflux for 16 hours. It was allowed to cool to room temperature and was filtered. The filtrate was concentrated by distilling off the solvent. The residue was taken up in 1,300 kg of toluene and the mixture was washed first with a mixture of 250 kg of water and 134 kg of concentrated hydrochloric acid and then again with 400 kg of water. After concentrating the mixture, 408 kg (61% of theory, relative to the 4-chlorophenol employed) of 1-(4-chlorophenoxy)-3,3-dimethyl-1-(1,2,4-triazol-1-yl)-butan-2-one were obtained as a viscous oil with a content of 66% (determined by gas chromatography).

It will be appreciated that the instant specification and examples are set forth by way of illustration and not limitation, and that various modifications and changes may be made without departing from the spirit and scope of the present invention.

We claim:

1. In the preparation of a phenoxy-azolyl-butanone derivative of the formula

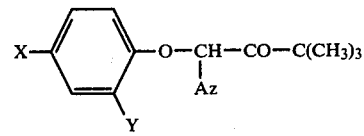

in which
X is a hydrogen atom,
Y is a hydrogen or halogen atom, and
Az is an imidazolyl radical or a 1,2,4-triazolyl radical,
wherein dichloropinacolin of the formula

is reacted with an azole of the formula

and a phenol of the formula

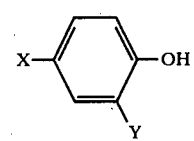

in the presence of an acid-binding agent, the improvement which comprises carrying out the reaction in the presence of a water-immiscible organic solvent at a temperature between about 40° and 150° C., and without isolation adding to the same water-immiscible solvent at a temperature between about 0° and +80° C. a mineral acid in amount sufficient to precipitate the mineral acid salt of the phenoxy-azolyl-butanone derivative, and separating such salt.

2. A process according to claim 1, wherein the water-immiscible organic solvent is a water-immiscible ketone.

3. A process according to claim 1, wherein the water-immiscible organic solvent is methyl isobutyl ketone.

4. A process according to claim 1, wherein the mineral acid is sulphuric acid.

5. A process according to claim 1, in which X is chlorine, Y is hydrogen or chlorine, and Az is a 1,2,4-triazol-1-yl radical.

6. A process according to claim 1, wherein the reaction of the dichloropinacolin with the azole is effected at a temperature between about 40° and 120° C.

7. A process according to claim 1, wherein the mineral acid is added at a temperature between about 20° and 70° C.

8. A process according to claim 1, wherein about 1 to 1.5 moles of dichloropinacolin, 1 to 1.5 moles of the azole and 1 to 4 moles of acid-binding agent are employed per mole of phenol.

9. A process according to claim 5, wherein the water-immiscible organic solvent is methyl isobutyl ketone, the mineral acid is sulphuric acid, the reaction of the dichloropinacolin with the azole is effected at a temperature between about 40° and 120° C., the mineral acid is added at a temperature between about 20° and 70° C., and about 1 to 1.5 moles of dichloropinacolin, 1 to 1.5 moles of azole and 1 to 4 moles of acid-binding agent are employed per mole of phenol.

* * * * *

UNITED STATES PATENT AND TRADEMARK OFFICE
CERTIFICATE OF CORRECTION

PATENT NO. : 4,388,465
DATED : Jun. 14, 1983
INVENTOR(S) : Hans-Ludwig Elbe et al It is certified that error appears in the above—identified patent and that said Letters Patent is hereby corrected as shown below:

Column 4, line 42, Delete "hydrogen" and insert --halogen--.

Signed and Sealed this

Twenty-seventh Day of September 1983

[SEAL]

Attest:

GERALD J. MOSSINGHOFF

Attesting Officer   Commissioner of Patents and Trademarks